United States Patent
Park et al.

(10) Patent No.: US 7,034,146 B2
(45) Date of Patent: Apr. 25, 2006

(54) PRIMER FOR DIAGNOSIS OF ONE OR MORE KINDS OF CANCER

(75) Inventors: Jong-Wook Park, Daegu (KR); Chang-Ho Jeon, Daegu (KR)

(73) Assignee: IC&G Co., Ltd., Taegu (KR)

( * ) Notice: Subject to any disclaimer, the term of this patent is extended or adjusted under 35 U.S.C. 154(b) by 334 days.

(21) Appl. No.: 10/258,828

(22) PCT Filed: Apr. 24, 2001

(86) PCT No.: PCT/KR01/00681

§ 371 (c)(1),
(2), (4) Date: Oct. 25, 2002

(87) PCT Pub. No.: WO01/81575

PCT Pub. Date: Nov. 1, 2001

(65) Prior Publication Data

US 2004/0023232 A1    Feb. 5, 2004

(30) Foreign Application Priority Data

Apr. 25, 2000 (KR) .................... 2000-21837

(51) Int. Cl.
*C07H 21/04* (2006.01)

(52) U.S. Cl. .................. 536/24.31; 536/24.3; 536/23.1

(58) Field of Classification Search ............ 536/23.1, 536/24.31, 24.3; 435/6, 91.2
See application file for complete search history.

(56) References Cited

U.S. PATENT DOCUMENTS

| 5,462,871 A | 10/1995 | Boon-Falleur et al. |
| 6,013,481 A | 1/2000 | DeBacker et al. |
| 6,057,105 A | 5/2000 | Hoon et al. |

FOREIGN PATENT DOCUMENTS

| WO | 98/46788 | * 10/1998 |

OTHER PUBLICATIONS

De Plaen et al. (Immunogenetics (1994) 40:360-369).*
Kariko (Bio Techniques, (Jun. 1995) 18 (6) 1048-9).*
Park et al. (Journal of Immunological Methods 266 (2002) 79-86).*
Maria Valeria Corrias et al., Expression of MAGE-1, MAGE-3 and MART-1 Genes in Neuroblastoma, Int. J. Cancer (Pred. Oncol) 69, 403-407 (1996).
T. Fujie et al., Expression of MAGE and BAGE genes in Japanese breast cancers, Annals of Oncology 8: 369-372, 1997.
Hiroshi Inoue et al., Human Esophageal Carcinomas Frequently Express the Tumor-Rejection Antigens of *MAGE* Genes, Int. J. Cancer: 63, 523-526 (1995).
Hiroshi Inoue et al., The Expression of Tumor-Rejection Anigen "*MAGE*" Genes in Human Gastric Carcinomas, Gastroenterology 1995;109:1522-1525.
Jian Lu, et al., Expression of the MAGE Gene Family in Human Gastric Carcinoma, Anticancer Research 17: 3559-3563 (1997).
Masaki Mori, M.D. et al., Expression of MAGE Genes in Human Colorectal Carcinoma, Annals of Surgery, vol. 224, No. 2 183-188 (1996).
Vincenzo Russo et al., MAGE, BAGE and GAGE genes expression in fresh epithelial ovarian carcinomas (Letter to the Editor) Int. J. Cancer, 67, 457-460 (1996).
Vincenzo Russo et al., Expression of the *MAGE* Gene Family in Primary and Metastatic Human Breast Cancer: Implications for Tumor Antigen-Specific Immunotherapy, Int. J. Cancer (Pred. Oncol.) 64, 216-221 (1995).
Shigeki Shichijo et al., Expression of the MAGE gene family in human lymphocytic leukemia, Cancer immunol Immunother (1995) 41: 95-103.
Benoit Van den Eynde et al., A New Family of Genes Coding for an Antigen Recognized by Autologous Cytolytic T Lymphocytes on a Human Melanoma, J. Exp. Med., The Rockefeller University Press, vol. 182, Spetember 1995 689-698.
P. Weynants et al., Expression of MAGE Genes by Non-Small-Cell Lung Carcinomas, Int. J. Cancer 56, 826-829 (1994).
Nobuyuki Yamashita et al., High Frequency of the *MAGE-1* Gene Expression in Hepatocellular Carcinoma, Hepatology vol. 24, No. 6, 1437-1440.

* cited by examiner

*Primary Examiner*—Juliet C. Switzer
(74) *Attorney, Agent, or Firm*—Orrick, Herrington & Sutcliffe

(57) ABSTRACT

This invention relates to primers for diagnosis of one or more kinds of cancer and a diagnostic kit comprising said primers. The primers are made from highly homologous areas of twelve MAGE subtypes and eight GAGE subtypes. The diagnostic kit comprising the said primers can detect six MAGE subtypes and eight GAGE subtypes respectively.

5 Claims, 6 Drawing Sheets

[FIG. 1]
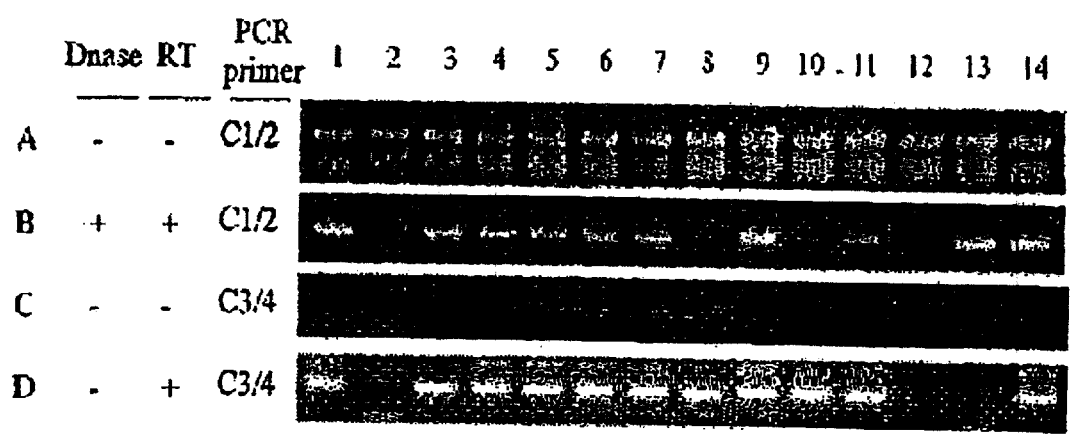
[FIG. 2]
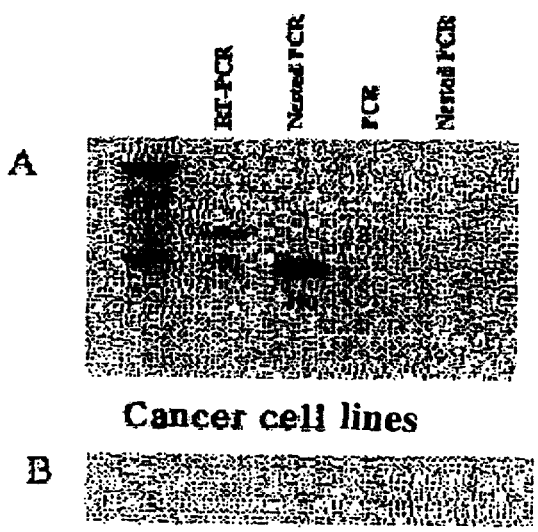
Cancer cell lines

[FIG. 3]

Cancer cell lines

| | 1 | 2 | 3 | 4 | 5 | 6 | 7 | 8 | 9 | 10 | 11 | 12 | 13 | 14 | Detection rate(%) |
|---|---|---|---|---|---|---|---|---|---|---|---|---|---|---|---|
| MAGE 1 | | | | | | | | | | | | | | | 50 |
| MAGE 2 | | | | | | | | | | | | | | | 35.7 |
| MAGE 3 | | | | | | | | | | | | | | | 57.1 |
| MAGE 4 | | | | | | | | | | | | | | | 35.7 |
| MAGE 5 | | | | | | | | | | | | | | | 7.1 |
| MAGE 6 | | | | | | | | | | | | | | | 14.2 |
| MAGE 1-6 | | | | | | | | | | | | | | | 78.6 |

[FIG. 4]

| | 1 | 2 | 3 | 4 | 5 | 6 | 7 | 8 | 9 | 10 | 11 | 12 | Detection rate(%) |
|---|---|---|---|---|---|---|---|---|---|---|---|---|---|
| MAGE-1 | | | | | | | | | | | | | 66.7 |
| MAGE-2 | | | | | | | | | | | | | 41.7 |
| MAGE-3 | | | | | | | | | | | | | 66.7 |
| MAGE-4 | | | | | | | | | | | | | 58.3 |
| MAGE-5 | | | | | | | | | | | | | 25.0 |
| MAGE-6 | | | | | | | | | | | | | 33.3 |
| MAGE 1-6 | | | | | | | | | | | | | 91.2 |

[FIG. 5]
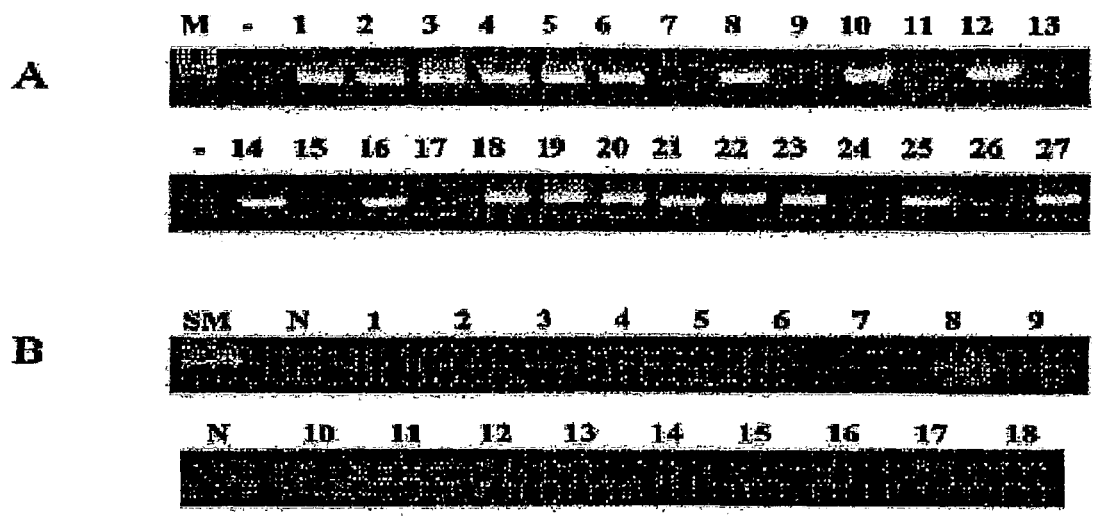
[FIG. 6]
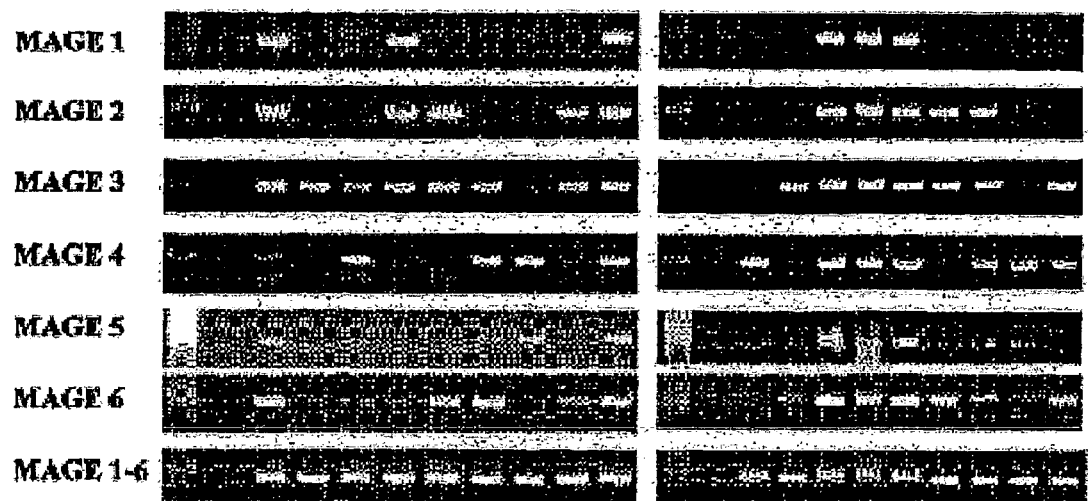

[FIG. 7]
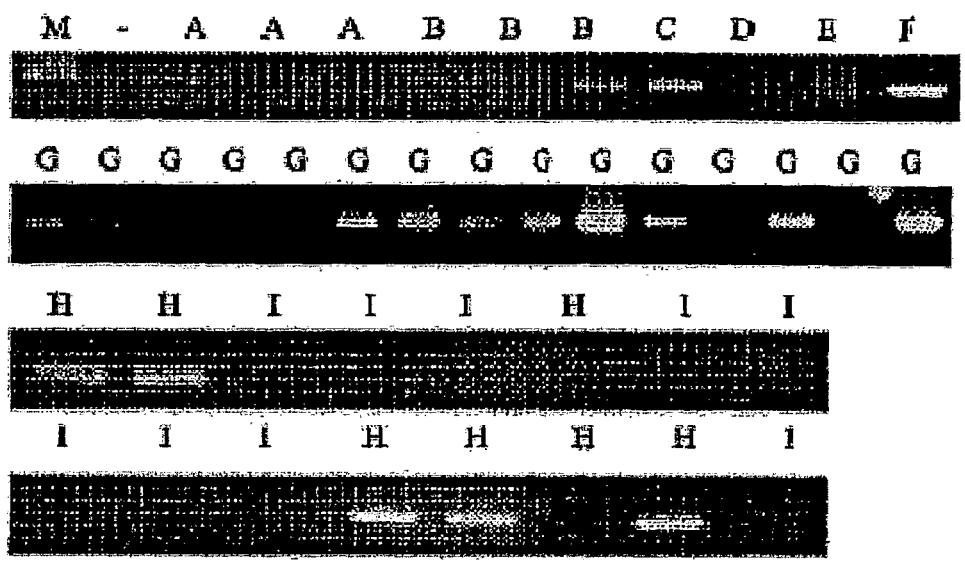
[FIG. 8]
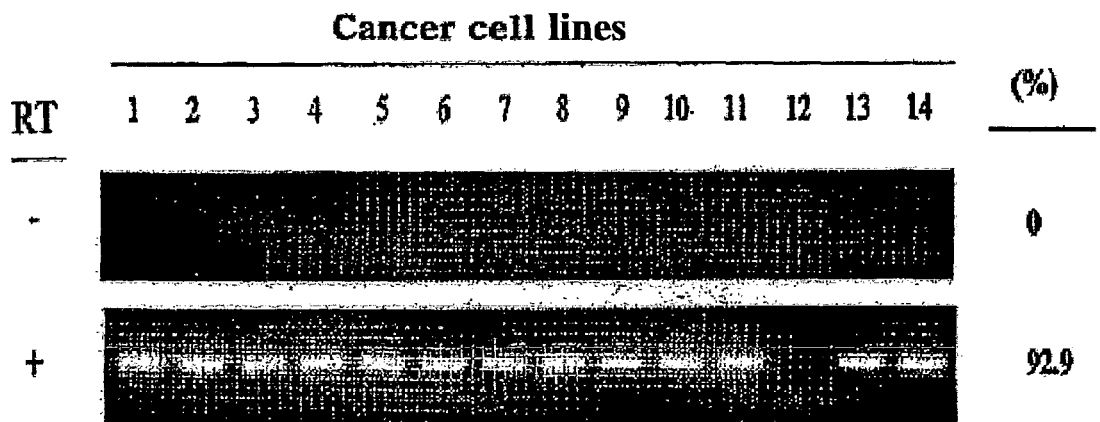

[FIG. 9]
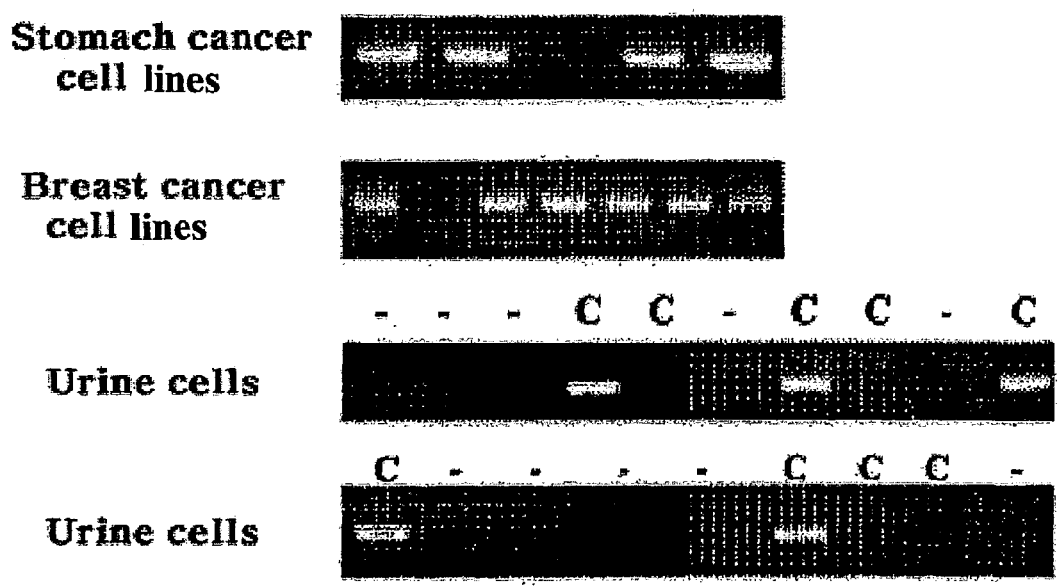
Stomach cancer cell lines
Breast cancer cell lines
Urine cells
Urine cells
[FIG. 10]
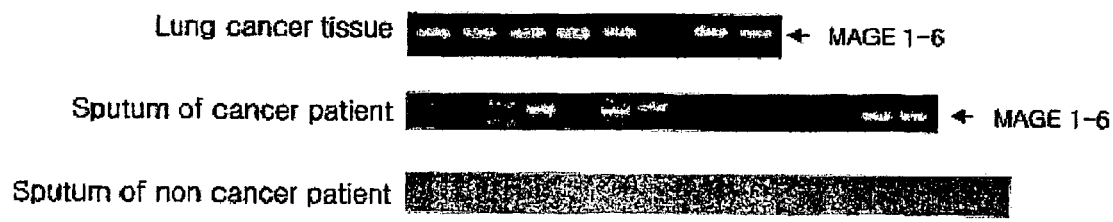
Lung cancer tissue ← MAGE 1-6
Sputum of cancer patient ← MAGE 1-6
Sputum of non cancer patient

[FIG. 11]
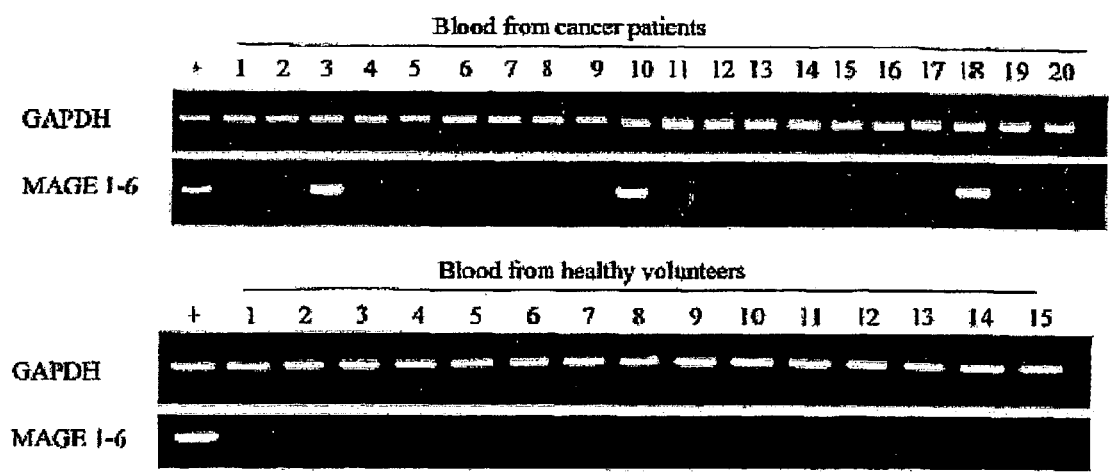

PRIMER FOR DIAGNOSIS OF ONE OR MORE KINDS OF CANCER

BACKGROUND OF THE INVENTION

1. Field of the Invention

The present invention is related to the primers for diagnosis of one or more kinds of cancers and a diagnostic kit containing the above primers, particularly to common primers that can simultaneously detect six MAGE sub-types from MAGE 1 to MAGE 6 (MAGE 1–6) or eight GAGE sub-types from GAGE 1 to GAGE 8 (GAGE 1–8) and a diagnostic kit containing the above common primers.

2. Description of the Prior Art

The diagnosis of cancers has been accomplished through the medical physical examination, X-ray and CT, histological examination, etc. However, these methods have not been appropriate for discrimination of a cancer among a cancer at its initial stage, a minute cancer, and a benign tumor.

However, the molecular biological diagnostic methods that have been developed recently have contributed greatly to the development of the cancer diagnostic area owing to their specificity in the diagnosis of cancers and their high sensitivity The most widely used method among many molecular biological diagnostic methods is the polymerase chain reaction (PCR) or the reverse transcriptase-polymerase chain reaction (RT-PCR). The abnormal gene, cancerous antigen gene, etc. of a sample are amplified and detected in these methods.

Particularly, RT-PCR is a method of detecting mRNA which is expressed in a particular gene. It may be used for the diagnosis of a cancer by examining the property of expression of cancerous antigen genes. The most important matter in the diagnosis of a cancer in the RT-PCR method is selection of a target gene for cancer diagnosis to be detected (hereinafter referred to as a "cancer diagnosis marker"). Generally, one cancer diagnosis marker is detected.

The requirements for a cancer diagnosis marker are that it should be expressed specifically in the cancer and that in a large amount in as many as possible cancers. MAGE (melanoma antigen gene) and GAGE are two kinds of cancer-associated testis antigens that are expressed in many kinds of cancer tissues but are not expressed in normal tissues except for the testis. It has been clarified that MAGE has been expressed in many cancers such as the stomach cancer (1, 2), esophagus cancer (3), colon cancer (4), lung cancer (5), breast cancer (6, 7), liver cancer (8), leukemia (9), neuroblastoma (10), ovary cancer (11), etc. in many studies since it was discovered in the melanoma. And it has been reported that GAGE has been expressed in the melanoma, sarcoma, small-cell carcinoma, head and neck cancer, bladder cancer, ovary cancer, etc. (11, 12). Therefore, MAGE and GAGE are very extensively utilized as cancer diagnostic markers since not only they can detect many kinds of cancers, not a simple kind of cancer, but also they have a high specificity for expression of cancer tissues compared to other cancer-associated antigens such as the carcinoembryonic antigen, etc. Also, MAGE and GAGE have a high homogeneity of genes among sub-types. About 12 kinds of sub-types of MAGE have the homogeneity ranging from about 56% to 99%, and 8 kinds of sub-types of GAGE have the homogeneity ranging from about 82% to 99%. Therefore, it is possible to increase the cancer diagnosis rate by using such same DNA sequence part as a primer since many sub-types of MAGE or GAGE may be detected simultaneously during RT-PCR.

Accordingly, common primers having a high cancer diagnostic rate and a high cancer diagnosis specificity through selection of MAGE or GAGE as a marker for cancer diagnosis and simultaneous detection of many sub-types of the marker for cancer diagnosis by RT-PCR are suggested in the present invention.

SUMMARY OF THE INVENTION

It is therefore an object of the present invention to provide with the primers for the diagnosis of cancers and a diagnostic kit containing such primers through simultaneous amplification of many sub-types of MAGEs or GAGEs and detection of these genes in RT-PCR.

The common primers are manufactured by comparing the gene sequences of many sub-types in order to detect many sub-types of MAGE and GAGE. The primers are manufactured by obtaining the information on 12 kinds of MAGE genes and 8 kinds of GAGE genes registered in GenBank, comparing the DNA sequence of each gene, analyzing the DNA homogeneity, and selecting a portion having a high homogeneity. The common primers thus manufactured are shown in Table 1 as follows:

TABLE 1

| Primer | Cancer diagnostic marker | Type | Sequence |
| --- | --- | --- | --- |
| Sequence No. 1 | MAGES 1-6 | S | 5'-GGTCACAAAGGCAGAAATGCT-3' |
| Sequence No. 2 | MAGES 1-6 | AS | 5'-GCCCTTGGACCCCACAGGAACTC-3' |
| Sequence No. 3 | MAGES 1-6 | S | 5'-CTGAAGGAGAAGATCTGCC-3' |
| Sequence No. 4 | MAGES 1-6 | AS | 5'-CTCCAGGTAGTTTTCCTGCAC-3' |
| Sequence No. 5 | MAGES 1-6 | S | 5'-CTGAAGGAGAAGATCTGCCWGTG-3' |
| Sequence No. 6 | MAGES 1-6 | AS | 5'-CCAGCATTTCTGCCTTTGTGA-3' |
| Sequence No. 7 | GAGES 1-8 | 5 | 5'-AGTTGGCGAGGAAGATCGAC-3' |
| Sequence No. 8 | GAGES 1-8 | AS | 5'-CTTCTTTTAACACTGTGATTGC-3' |
| Sequence No. 9 | GAGES 1-8 | S | 5'-AGCCTCCTGAARTGATTGG-3' |
| Sequence No. 10 | GAGES 1-8 | AS | 5'-GCGTTTTCACCTCCTCTGGAT-3' |

In Table 1, S means a sense primer, AS means an anti-sense primer, W means A or T, and R means A or G.

Sequence No. 1/2 is the primer for MAGE, but shows a false positive reaction in PCR. It is suspected that the reason for a false positive reaction is that it is very likely that the genes are amplified from the contaminated generic DNA since these primers are located in one exon.

Sequence No. 3/4 and Sequence No. 5/6 are the primers for MAGE. Sequence No. 3 and Sequence No. 5 are the primers that are located at the boundary of two exons. No false positive reaction is shown on PCR and nested PCR using Sequence No. 3/4 and Sequence No. 5/6 since Sequence No. 3 and Sequence No. 5 does not bind to the genoric DNA.

Sequence No. 7/8 and Sequence No. 9/10 are the primers for GAGE. Sequence No. 7 and Sequence No. 8 or Sequence No. 9 and Sequence No. 10 are located at difference exons, and no false positive reaction is shown in the experiments in which Sequence No. 7/8 and Sequence No. 9/10 are used since a long intron is inserted between these exons.

The cell lines used for the diagnosis of cancers include the human stomach cancer cell line (SNU484, SNU638, SNU668), head and neck cancer cell line (AMC-HN-3, AMC-HN-4, AMC-HN-7), cervix cancer cell line (HeLa, Caski), lung cancer cell line (NCI H1703, NCI H522), colon cancer cell line (HT29), metastatic prostate gland cancer cell line (LN.CAP), and promyelocytic leukemia (HL60) and osteosarcoma cell line (SaOS2). And for the human body cancer tissues and cells, 12 cases of breast cancer, 27 cases of head and neck cancer, 5 cases of stomach cancer, 3 cases of thyroid gland cancer, 3 cases of lymphoma, 1 case of cystic adenoma, 1 case of sarcoma, 1 case of dermatofibrosarcoma, 1 case of malignant mixed tumor, 9 cases of urine cells of the patients of bladder cancer, and 15 cases of abdominal cavity cells of the patients of stomach cancer are used. For the reference benign tumor tissues and cells, 18 cases of benign head and neck tumor, 10 cases of normal white blood cells, and 10 case of urine cells of normal people and of patients of urologic inflammation are used.

Various cancer tissues are kept at −70° C. until they are used, and are pulverized with a grinder after adding RNAzol B (Tel-Test Inc., U.S.A.), to the tissues.

The cultured cancer cell lines are dissolved by adding RNAzol B after completely removing the culture medium and washing with the phosphate buffered saline (PBS) solution. The abdominal cavity cells of stomach cancer are collected after opening the abdominal cavity and are mixed with RNAzol B. The normal white blood cells are dissolved completely by adding RNAzol B after only nucleated cells are collected from the blood. The urine cells are mixed with RNAzol B after the cells are collected from the urine.

Separation of RNA from the RNAzol B solution in which various tissues and cells are dissolved is done according to the manufacturer's instructions (Tel-Test., U.S.A.).

The sputum is used for RT-PCR after it is liquefied by adding the equivalent amount of a stabilizer (Roche Diagnostics, Malinheim, Germany) and mixing thoroughly, and MnRNA is separated by using the mRNA separation reagent (Roche Diagnostics, Mahnheim, Germany).

PCR may be used for the diagnosis of cancers by using the common primers of the present company. cDNA is produced by the reverse transcriptase (RT) reaction after extracting the total RNA or MRNA from various cancer tissues, sputum, blood, urine, abdominal cavity cells, etc. of the patients. MAGE 1–6 or GAGE 1–8 are amplified by performing PCR using the common primers of the present invention (Sequence No. 1 and 2 or Sequence No. 3 and 4 or Sequence No. 7 and 8) for cDNA. Many kinds of cancers may be diagnosed simultaneously through detection of MAGE 1–6 or GAGE 1–8 DNA bands by electrophoresis of the product of PCR after performing the secondary PCR (nested PCR) using the common primers of the present invention (Sequence No. 5 and 6 or Sequence No. 9 and 10) for the primary product of RT-PCR.

In the present invention, RT-PCR is used as a method of amplification of MAGE 1–6 or GAGE 1–8. However, it is not limited to the applications described in the present specification, and various methods of amplification of MAGE 1–6 or GAGE 1–8 by using the common primers of the present invention are included in as much as it has various applications by varying the reagents, cycles, etc. by the experimenter.

A cancer diagnostic kit including the common primers of the present invention and PCR or RT-PCR reagents may be provided with in the present invention.

BRIEF DESCRIPTION OF THE DRAWINGS

The foregoing and other objects, aspects and advantages will be better understood from the following detailed description of a preferred embodiment of the invention with reference to the drawings, in which:

FIG. 1 shows the affects of processing of MAGE primers and DNase on the detection of MAGE using PCR or RT-PCR;

FIG. 2 shows the results of the specificity of detection of MAGE using the RT-PCR method of Sequence No. 3/4 and Sequence No. 5/6 primers;

FIG. 3 shows the results of measuring each sub-type of MAGE and MAGE 1–6 by using Sequence No. 3/4 and Sequence No. 5/6 primers in the cancer cell lines;

FIG. 4 shows the results of measuring each sub-type of MAGE and MAGE 1–6 by using Sequence No. 3/4 and Sequence No. 5/6 primers in the cancer tissues of the patients of breast cancer;

FIG. 5 shows the results of measuring MAGE 1–6 by using Sequence No. 3/4 and Sequence No. 5/6 primers in the head and neck cancer and benign head and neck tumor;

FIG. 6 shows the results of measuring each sub-type of MAGE and MAGE 1–6 by using Sequence No. 3/4 and Sequence No. 5/6 primers in the cancer tissues of the patients of head and neck cancer;

FIG. 7 shows the results of measuring MAGE 1–6 by using Sequence No. 3/4 and Sequence No. 5/6 primers in other cancer tissues and urine cells;

FIG. 8 shows the results of measuring GAGE 1–8 by using Sequence No. 7/8 and Sequence No. 9/10 primers in the cancer cell lines;

FIG. 9 shows the results of measuring GAGE 1–8 by using Sequence No. 7/8 and Sequence No. 9/10 primers in the cancer tissues and urine cells;

FIG. 10 shows the results of measuring MAGE 1–6 by using Sequence No. 3/4 and Sequence No. 5/6 primers in the lung cancer tissues and sputum; and FIG. 11 shows the results of measuring MAGE 1–6 by using Sequence No. 3/4 and Sequence No. 5/6 primers in the blood.

DETAILED DESCRIPTION OF A PREFERRED EMBODIMENT OF THE INVENTION

The present invention is illustrated in more details below although the content of the present invention is not limited to the followings:

Firstly, the gene expression of MAGE and GAGE and the manufacture of primers are illustrated.

The DNA sequences are compared and analyzed by using the DNAsis program after obtaining the information on 12 kinds of MAGE genes and 8 kinds of GAGE genes registered in GenBank. It is shown that the homogeneity of genes of the MAGE type (cDNA) is 56%–99% and the homogeneity of genes of the GAGE type (cDNA) is 82%–99%. The portions having the same or similar DNA sequence of each sub-type are designed to be the primers.

The synthesis is completed after mounting dATP, dTTP, dCTP, and dGTP which are the materials for primer synthesis and the columns for synthesis to the automatic DNA synthesizer (Expedite TM Nucleic Acid Synthesis System of PerSeptive Biosystem Company) and inputting the sequence to be synthesized. The synthesized primers are used by measuring their concentrations with a UV spectrophotometer after the animonia processing procedure and refining procedure. The primers thus manufactured are shown in Table 1.

Sequence No. 1 and Sequence No. 2 (Sequence No. 1/2) and Sequence No. 3 and Sequence No. 4 (Sequence No. 3/4) are the MAGE primers and are used for RT-PCR or the primary PCR, and Sequence No. 5 and Sequence No. 6 (Sequence No. 5/6) are used for the secondary PCR (nested PCR).

Sequence No. 7 and Sequence No. 8 (Sequence No. 7/8) and Sequence No. 9 and Sequence No. 10 (Sequence No. 9/10) are the primers for the detection of GAGEs, where Sequence No. 7/8 is used for RT-PCR or the primary PCR, and Sequence No. 9/10 is used for the nested PCR.

Secondly, the procedures for separation of the total RNA are described below:

Various cancer tissues are kept at −70° C. before they are used. The tissues are pulverized with a grinder after adding 1–2 ml of RNAzol B (Tel-Test Inc., U.S.A.) to the tissues. The cultivated cancer cell lines are separated by adding RNAzol B after completely removing the culture medium and washing culture plate once with the PBS. The abdominal cavity cells of stomach cancer are collected through centrifugal separation at 1,200 rpm for 5 minutes after collecting the abdominal cavity cells by adding 100 ml of physiological saline solution to the lower abdominal cavity after opening the abdominal cavity. After the cells are washed once with the PBS, they are mixed by adding RNAzol B to the cell pellet. In the separation of normal white blood cells, only nucleated cells are collected through centrifugal separation at 1,200 rpm for 5 minutes after letting them stand still for 17 seconds after adding 20 ml of sterilized distilled water (DEPC-DW) to 5 ml of the blood containing an anticoagulant and mixing by adding 20 ml of the twice concentrated PBS. The cells are dissolved completely by adding 1 ml of RNAzol B to the cells collected. The urine cells are collected through centrifugal separation of 150 ml of urine. The cells are washed once by adding the PBS and are mixed with 1 ml of RNAzol B.

The protein layer and RNA are separated from each other through centrifugal separation at 12,000 rpm for 15 minutes after adding the 1/10 portion of chloroform to the RNAzol B solution in which various tissues and cells are dissolved and mixing them thoroughly. And the RNA solution of the separated supernatant is collected carefully and transferred into a 1.5-ml test tube. RNA is precipitated by adding 100% isopropanol in the same amount to the RNA solution, mixing, and keeping at −20° C. for longer than 16 hours. Then RNA is precipitated through centrifugal separation of the mixed RNA-isopropanol solution at 12,000 rpm, the supernatant is removed, RNA precipitates are washed by adding 1 ml of 70% cold ethanol to the above, and the upper ethanol solution is removed completely through centrifugal separation, RNA precipitates are dissolved into the sterilized distilled water (DEPC-DW), and the concentration and purity of RNA are measured by using a spectrophotometer. A part of reagents is processed at 37° C. for 1 hour by adding 100 μg of RNA to the DNase solution (20-mM $MgCl_2$, 20-mM tris-HCL, 0.4-U DNase 1, 0.8-U RNasin), and RNA is extracted again and is used for RT-PCR or RNA PCR as described in the above.

The sputum is completely liquefied by adding a stabilizer (Roche Diagnostics, Mahnheim, Germany) in the same amount and mixing thoroughly, and mRNA is separated by using a separation reagent (Roche Diagnostics, Mahnheim, Germany)) and is used for RT-PCR.

Thirdly, the total RNA is collected and PCR is performed as follows in order to see if the genomic MAGE DNA is contaminated. In the first step, the PCR reaction solution is made by mixing 3 μl of the 10×PCR buffer solution, 1.8 μl of 250-mM $MgCl_2$, 0.3 μl of 10-mM dATP, 0.3 μl of 10-mM dGTP, 0.3 μl of 10-mM dTTP, 0.3 μl of 10-mM dCTP, 0.25 μl of 50-μM sense and anti-sense primers, and 0.25 μl of the Taq polymerase (5 U/μl, Promega Co., U.S.A.) to make up 25 μl of the final PCR reaction solution. The PCR reaction solution is put into a PCR tube, 5 μl of the total RNA solution (0.1 μg/μl) is added to the above solution and mixed, 1 drop of a mineral oil is dropped, and the entire solution is put into a PCR machine (Cetus 480, Perkin Elmer Co., U.S.A.) in order to perform PCR under the following conditions: Firstly, DNA is denatured by heating the above solution at 94° C. for 5 minutes and reacting for 30–35 cycles in which 1 cycle is for 30 seconds at 94° C., 45 seconds at 57° C., and 45 seconds at 72° C., and PCR is completed by treating the above solution at 72° C. for 5 minutes finally. Then the amplified DNA bands are observed by using a UV transilluminator after adding the product of PCR to 1% agarose gel and electrophoresis.

Fourthly, the reverse transcriptase-polymerase chain reaction (RT-PCR) is performed. RNA is denatured by keeping the total RNA solution in a 70° C. water bath for 10 minutes and kept in ice. Firstly, 2 μl of the 5×RT buffer solution, 0.25 μl of 10-mM dATP, 0.25 μl of 10-mM dGTP, 0.25 μl of 10-mM dTTP, 0.25 μl of 10-mM dCTP, 0.25 μl of MMLV reverse transcriptase (200U/μl ), 0.25 μl of RNase inhibitor (28 U/μl ), 0.5 μl of 50μM oligo dT primer, and 4 μl of the sterilized distilled water (DEPC-DW) are put into a PCR tube in order to make an RT reaction solution. To the RT reaction solution, 2 μl of the total RNA solution (1 μg/μl) that is kept in ice is added and 1 drop of a mineral oil is dropped, and the entire solution is kept at a room temperature for 10 minutes. The reverse transcriptase reaction is completed by putting this test tube into the PCR machine and treating with heat at 42° C. for 60 minutes. And the product of reverse transcriptase reaction is diluted with distilled water at the ratio of 1:1 and is used for PCR. PCR is performed under the following conditions by adding 5 μl of the product of reverse transcriptase reaction into 25 μl of the PCR reaction solution as described in the above, mixing them, dropping 1 drop of a mineral oil, and putting the solution into the PCR machine: Firstly, DNA is denatured by heating the solution at 94° C. for 5 minutes and reacting for 18–35 cycles in which 1 cycle is for 30 seconds at 94° C., 45 seconds at 57° C., and 45 seconds at 72° C., and PCR is completed by processing the above at 72° C. for 5 minutes finally.

Fifthly, in the nested PCR, the product of PCR or RT-PCR reaction is diluted 10 times with distilled water, its 5-μl portion is taken, and the secondary PCR is performed after adding PCR reagents as described in the above.

Sixthly, the affects of processing of the MAGE primer and DNase on the detection of MAGE are reviewed.

The total RNA is extracted from the cultured stomach cancer cell line (SNU484, SNU638, SNU668), head and neck cancer cell line (AMC-HN-3, AMC-HN-4, AMC-HN-7), cervix cancer cell line (HeLa, Caski), lung cancer cell line (NCI H1703, NCI H522), colon cancer cell line (HT29), metastatic prostate gland cancer cell line (LN.CAP), and promyelocytic leukemia (HL60) and osteosarcoma cell line (SaOS2), after which PCR and RT-PCR for detecting MAGE are performed. (Refer to FIG. 1.)

A in FIG. 1 is the result of PCR of the total RNA by using Sequence No. 1/2, and B is the result of PCR of the total RNA by using Sequence No. 1/2 after processing DNase to the total RNA. C is the result of PCR of the total RNA by using Sequence No. 3/4, and D is the result of PCR of the total RNA by using Sequence No. 3/4 and further of nested PCR by using Sequence No. 5/6. In conclusion, it is necessary to perform DNase processing in order to use Sequence No. 1/2, but MAGE may be detected without DNase processing by Sequence No. 3/4 and Sequence No. 5/6, and no false positive reaction by the amplification of genomic DNA is shown. And Sequence No. 3/4 and Sequence No. 5/6 may detect at least one of 6 kinds of sub-types of MAGE (MAGE 1–6) from MAGE 1 to MAGE 6.

Seventhly, the cancer diagnosis specificity of the RT-PCR method by using Sequence No. 3/4 and Sequence No. 5/6 is evaluated. In order to study the specificity of the RT-PCR method by using Sequence No. 3/4 and Sequence No. 5/6, the SNU484 cell line and normal white blood cells are extracted to perform RT-PCR and nested PCR. The results show that MAGE 1–6 are detected only in RT-PCR and nested PCR in SNU484, and generic DNA is not amplified when PCR and nested PCR are performed. (Refer to FIG. 2A.) Further, no MAGE 1–6 is detected in normal white blood cells. (Refer to FIG. 2B.)

Eighthly, in the measurement of MAGEs in the cancer cell line, each sub-type of MAGE and MAGE 1–6 are measured for 14 kinds of cancer cell lines. Each sub-type of MAGE is detected by RT-PCR using Sequence No. 3 and MAGE sub-type specific primers. MAGE 1–6 is detected by RT-PCR using Sequence No. 3/4 and nested PCR using Sequence No. 5/6. The experiments for measuring MAGE 1–6 show a higher positive rate (78.6%) compared to that in the measurement of each sub-type. (Refer to FIG. 3.)

Ninthly, in the measurement of MAGEs in the breast cancer, each sub-type of MAGE and MAGE 1–6 are measured for the cancer tissues of the patients of breast cancer. RT-PCR having Sequence No. 3/4 as primer and nested PCR using the Sequence No. 5 primer and MAGE sub-type specific primer are performed, but RT-PCR using Sequence No. 3/4 and nested PCR using Sequence No. 5/6 are performed for the detection of MAGE 1–6. A higher positive rate (91.2%) is shown in the measurement of MAGE 1–6 compared to that in the measurement of each sub-type. (Refer to FIG. 4.)

Tenthly, in the measurement of MAGEs in the head and neck cancer and benign head and neck tumor, MAGE 1–6 are measured. MAGE 1–6 is measured by RT-PCR using Sequence No. 3/4 and nested PCR using Sequence No. 5/6. Among 27 cases of cancers, 19 cases are positive (70.3%), and none is detected in the benign tumor. (Refer to FIG. 5, where M means a size marker and—is PCR without adding CDNA.)

Eleventhly, in the measurement of MAGE sub-types in the head and neck cancers, each sub-type of MAGE and MAGE 1–6 are measured in the samples in which MAGE 1–6 are detected among the samples of head and neck cancer. RT-PCR using Sequence No. 3/4 as a primer and nested PCR using the Sequence No. 5 and MAGE sub-type specific primers are performed, and MAGE 1–6 are measured in terms of RT-PCR and nested PCR by using Sequence No. 3/4 and Sequence No. 5/6, respectively. The method of measurement of each sub-type has a lower efficiency than that of the method of detection of MAGE 1–6. (Refer to FIG. 6.)

Twefthly, the measurement of MAGE 1–6 in other cancer tissues and abdominal cavity and urine cells is reviewed.

MAGE 1–6 are measured in terms of RT-PCR and nested PCR by using Sequence No. 3/4 and Sequence No. 5/6, respectively. The objects of measurement include the thyroid gland cancer (A), lymphoma (B), cystic adenoma (C), sarcoma (D), dermatofibrosarcoma (E), malignant mixed tumor (F), abdominal cavity cell of the patients of stomach cancer (G), urine of the patients of bladder cancer (H), and urine of the patients of other diseases (I). (Refer to FIG. 7, where M means a size marker, and—is PCR without adding cDNA.)

No MAGE 1–6 are detected in the thyroid gland cancer, but various kinds of MAGEs are detected in the abdominal cells of the patients of remaining cancers and stomach cancer and the urine cells of the patients of bladder cancer.

Thirteenthly, in the measurement of GAGEs in cancer tissues and urine cells, GAGE 1–8 of 14 kinds of cancer cell lines are measured. GAGE 1–8 are measured in terms of RT-PCR or PCR using Sequence No. 7/8 or nested PCR using Sequence No. 9/10.

No GAGE is detected in case of PCR and nested PCR without the reverse transcriptase reaction, and positive reactions are shown in 13 reactions axnong 14 reactions (92.9%) in case of PCR and nested PCR after the reverse transcriptase reaction. (Refer to FIG. 8.) In the stomach cancer, 80% of reactions are shown to be positive to GAGEs, 85.7% is shown to be positive in breast cancer, and 55.6% is shown to be positive in the urine cells of bladder cancer. And no positive reactions are shown in the urine of the patients of diseases other than the cancer. (Refer to FIG. 9.)

Fourteenthly, in the measurement of MAGEs in the lung cancer tissues and sputum, MAGE 1–6 are measured in 8 cases of lung cancer tissues, 14 cases of sputum of the patients of lung cancer, and 16 cases of sputum of hospitalized patients of diseases other than the lung cancer. They are measured in terms of RT-PCR and nested PCR by using Sequence No. 3/4 and Sequence No. 5/6, respectively. MAGE 1–6 are detected in 7 cases among 8 cases of lung cancer tissues, and 4 cases among 14 cases of sputum of the patients of lung cancer. And no MAGEs are detected at all in 16 cases of sputum of hospitalized patients of diseases other than the lung cancer. (Refer to FIG. 10.)

Fifteenthly, in the measurement of MAGEs in the blood, MAGEs are measured in 20 cases of the blood of patients of cancer and 15 cases of the blood of normal people. They are measured in terms of RT-PCR and nested PCR by using Sequence No. 3/4 and Sequence No. 5/6, respectively. MAGE 1–6 are detected in 3 cases among 20 cases of the blood of the patients of cancer, and none is detected in the blood of normal people. (Refer to FIG. 11, where + is a sample in which 5 cells of SNU484 (MAGEs 1–6 benign cells) to 5 ml of the blood of normal people.)

Primer Sequence 3/4 an Sequence No. 5/6 that detect MAGE 1 to MAGE 6 simultaneously and Sequence No. 7/8 and Sequence No. 9/10 that detect GAGE 1 to GAGE 8 simultaneously may be used as cancer diagnostic kits having a high specificity and a high diagnosis rate of cancer compared to the method of measuring each sub-type.

Also, they not only have a very high specificity for the diagnosis of cancers since none is shown to be positive in various normal cells and benign tumors, but also can detect MAGEs in urine cells or sputum cells by using these common primers. Therefore, they may be used for cancer diagnostic kits for non-hygroscopic samples, as well as tissues. The present invention is also advantageous in that the time and expenses may be reduced through simultaneous measuring of many sub-types of MAGEs or GAGEs.

References

1) Li J, Yang Y, Fujie T, Tanaka F, Mimori K, Haraguchi M, Ueo H, Mori M, and Akiyoshi T, "Expression of the MAGE gene family in human gastric carcinoma," Anticancer Res. 17:3559–3563, 1997.
2) Inoue H. Li J, and Honda M, "MAGE-1 MnRNA expression in gastric carcinoma," Gastroenterol 109: 1522–1525, 1995.
3) Inoue H, Mori M, and Honda M, "Human esophageal carcinomas frequently expressing the tumor-rejection antigens of MAGE genes," Inf J-Cancer 63: 523–526, 1995.
4) Mori M, lnoue H, and Mimori K, "Expression of MAGE genes in human colorectal carcinoma," Ann Surg 224: 183–188, 1996.
5) Weynants P, Lethe B, Brasseur F, Marchand M, and Boon T, "Expression of MAGE genes by non-small cell lung carcinomas," Int J Cancer 56: 826–829, 1994.
6) Russo M, Traversari C, and Verrecchia A, "Expression of MAGE gene family in primary and metastatic human breast cancer: Implications for tumor-specific immunotherapy," Int J Cancer 64: 216–221, 1995.
7) Fujie T, Mori M, Ueo H, Sugimachi K, and Akiyoshi A, "Expression of MAGE and BAGE genes in Japanese breast cancers," Ann Oncol 8: 369–372, 1997.
8) Yamashita N, Ishibashi H, Hayashida K, Kudo J, Takenaka K, Itoh K, and Niho Y, "High frequency of the MAGE-1 gene expression in hepatocellular carcinoma," Hepatology 24: 1437–1440, 1996.
9) Shichijo S, Tsunosue R, Masuoka K, Natori H, Tamai M, Miyajima J, Sagawa K, and Itoh K, "Expression of the MAGE gene family in human lymphocytic leukemia," Cancer Immunol Immunother 41: 90–103, 1995.
10) Corrias M V, Scaruffi P, Occhino M, De Bemardi B, Tonini G P, and Pistoja V, "Expression of MAGE-1, MAGE-3 and MART-1 genes in neuroblastoma," Int J Cancer 69: 403–407, 1995.
11) Russo V, Dalerba P. Ricci A, Bonazzi C, Leone B E, Mangioni C, Allavena P, Bordignon C, and Traversari C, "MAGE, BAGE and GAGE genes expression in fresh epithelial ovarian carcinomas," Int J Cancer 67: 457–460, 1996.
12) Van den Eynde B, Peeters O, De Backer B, Gaugler S, Lucas, and Boon T, "A new family of genes coding for an antigen recognized by autologous cytolytic T lymphocytes on a human melanoma," J Exp Med 182: 689, 1995.

What is claimed is:

1. A primer selected from the group of primers consisting of SEQ ID NO: 3 and SEQ ID NO: 5.

2. A set of primers, wherein the set includes a primer pair selected from the group consisting of the primer pair SEQ ID NO: 3 and SEQ ID NO: 4 and the primer pair SEQ ID NO: 5 and SEQ ID NO: 6, or wherein the set of primers includes both pairs.

3. A cancer diagnostic kit, wherein the main component of said cancer diagnostic kit is a set of primers, wherein the set includes a primer pair selected from the group consisting of the primer pair SEQ ID NO: 3 and SEQ ID NO: 4 and the primer pair SEQ ID NO: 5 and SEQ ID NO: 6, or wherein the set of primers includes both pairs.

4. A cancer diagnostic kit containing a primer selected fiom the group of primers consisting of SEQ ID NO: 3 and SEQ ID NO: 5 or containing a both primers.

5. A cancer diagnostic kit containing a set of primers, wherein the set includes a primer pair selected from the group consisting of the primer pair SEQ ID NO: 3 and SEQ ID NO: 4 and the primer pair SEQ ID NO: 5 and SEQ ID NO: 6, or wherein the set of primers includes both pairs.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: primer targeting MAGE 1-6; sense primer type

<400> SEQUENCE: 1
ggtcacaaag gcagaaatgc t                                              21

<210> SEQ ID NO 2
<211> LENGTH: 23
<212> TYPE: DNA
<213> ORGANISM: Artificial Sequence
<220> FEATURE:
<223> OTHER INFORMATION: primer targeting MAGE 1-6; antisense primer
      type

<400> SEQUENCE: 2
gcccttggac cccacaggaa ctc                                            23

<210> SEQ ID NO 3
<211> LENGTH: 19
<212> TYPE: DNA
<213> ORGANISM: Artificial Sequence
<220> FEATURE:
<223> OTHER INFORMATION: primer targeting MAGE 1-6; sense primer type
```

-continued

```
<400> SEQUENCE: 3
ctgaaggaga agatctgcc                                                    19

<210> SEQ ID NO 4
<211> LENGTH: 21
<212> TYPE: DNA
<213> ORGANISM: Artificial Sequence
<220> FEATURE:
<223> OTHER INFORMATION: primer targeting MAGE 1-6; antisense primer
      type

<400> SEQUENCE: 4
ctccaggtag ttttcctgca c                                                 21

<210> SEQ ID NO 5
<211> LENGTH: 23
<212> TYPE: DNA
<213> ORGANISM: Artificial Sequence
<220> FEATURE:
<223> OTHER INFORMATION: primer targeting MAGE 1-6; sense primer type

<400> SEQUENCE: 5
ctgaaggaga agatctgccw gtg                                               23

<210> SEQ ID NO 6
<211> LENGTH: 21
<212> TYPE: DNA
<213> ORGANISM: Artificial Sequence
<220> FEATURE:
<223> OTHER INFORMATION: primer targeting MAGE 1-6; antisense primer
      type

<400> SEQUENCE: 6
ccagcatttc tgcctttgtg a                                                 21

<210> SEQ ID NO 7
<211> LENGTH: 20
<212> TYPE: DNA
<213> ORGANISM: Artificial Sequence
<220> FEATURE:
<223> OTHER INFORMATION: primer targeting GAGE 1-6; sense primer type

<400> SEQUENCE: 7
agttggcgag gaagatcgac                                                   20

<210> SEQ ID NO 8
<211> LENGTH: 22
<212> TYPE: DNA
<213> ORGANISM: Artificial Sequence
<220> FEATURE:
<223> OTHER INFORMATION: primer targeting GAGE 1-6; antisense primer
      type

<400> SEQUENCE: 8
cttcttttaa cactgtgatt gc                                                22

<210> SEQ ID NO 9
<211> LENGTH: 19
<212> TYPE: DNA
<213> ORGANISM: Artificial Sequence
<220> FEATURE:
<223> OTHER INFORMATION: primer targeting GAGE 1-6; sense primer type
```

```
<400> SEQUENCE: 9
agcctcctga artgattgg                                                19

<210> SEQ ID NO 10
<211> LENGTH: 21
<212> TYPE: DNA
<213> ORGANISM: Artificial Sequence
<220> FEATURE:
<223> OTHER INFORMATION: primer targeting GAGE 1-6; antisense primer
      type

<400> SEQUENCE: 10
gcgttttcac ctcctctgga t                                             21
```